US012059326B2

(12) United States Patent
Rodzewicz et al.

(10) Patent No.: US 12,059,326 B2
(45) Date of Patent: Aug. 13, 2024

(54) MEDICAL DRESSING

(71) Applicant: Mölnlycke Health Care AB, Gothenburg (SE)

(72) Inventors: Patrick Rodzewicz, Gothenburg (SE); Linda Mårlind, Kullavik (SE); Dennis Hansson, Gunnilse (SE); Karin Glasmästar, Hisings Backa (SE); Anna Grou, Gothenburg (SE); Conny Jakobsson, Lerum (SE); Océane Lançon, Säve (SE)

(73) Assignee: Mölnlycke Health Care AB, Gothenburg (SE)

( * ) Notice: Subject to any disclaimer, the term of this patent is extended or adjusted under 35 U.S.C. 154(b) by 921 days.

(21) Appl. No.: 16/770,175

(22) PCT Filed: Dec. 13, 2018

(86) PCT No.: PCT/EP2018/084744
§ 371 (c)(1),
(2) Date: Jun. 5, 2020

(87) PCT Pub. No.: WO2019/115686
PCT Pub. Date: Jun. 20, 2019

(65) Prior Publication Data
US 2020/0383839 A1    Dec. 10, 2020

(30) Foreign Application Priority Data
Dec. 15, 2017    (EP) .................................... 17207756

(51) Int. Cl.
*A61F 13/06*    (2006.01)
*A61F 13/00*    (2024.01)

(52) U.S. Cl.
CPC .. *A61F 13/069* (2013.01); *A61F 2013/00608* (2013.01); *A61F 2013/00655* (2013.01)

(58) Field of Classification Search
CPC ................ A61F 13/025; A61F 13/0209; A61F 13/0223; A61F 13/023; A61F 13/0253;
(Continued)

(56) References Cited

U.S. PATENT DOCUMENTS

2005/0059918 A1    3/2005  Sigurjonsson et al.
2017/0135862 A1*   5/2017  Tuck ..................... A61L 31/028

FOREIGN PATENT DOCUMENTS

EP    2001424 A2    12/2008
EP    3085344 A1 *  10/2016  ......... A61F 13/0209
(Continued)

OTHER PUBLICATIONS

International Search Report and Written Opinion were mailed on Mar. 6, 2019 by the International Searching Authority for International Application No. PCT/EP2018/084742, filed on Dec. 13, 2018 and published as WO 2019/115685 on Jun. 20, 2019 (Applicant—Molnlycke Health Care AB) (11 Pages).
(Continued)

*Primary Examiner* — Ophelia A Hawthorne
(74) *Attorney, Agent, or Firm* — Ballard Spahr LLP

(57) ABSTRACT

A medical dressing for prevention of pressure ulcers is described. The dressing has a backing layer, a pad, and a body contact layer, wherein the pad is arranged between the backing layer and the body contact layer. The body contact layer has an adhesive skin contact layer and an anisotropic layer having a first (x) direction and a second (y) direction perpendicular to the first (x) direction. The anisotropic layer is stiffer in the second (y) direction than in the first (x) direction. The dressing reduces shear and compression forces on the skin and in the underlying soft tissue layers and prevents the onset of pressure ulcers.

14 Claims, 10 Drawing Sheets

(58) Field of Classification Search
CPC .............. A61F 13/00068; A61F 13/069; A61F 2013/00608; A61F 2013/00655; A61F 13/0246; A61F 13/0203; A61F 13/00; A61L 31/028
See application file for complete search history.

(56) References Cited

FOREIGN PATENT DOCUMENTS

| EP | 3260098 A1 | 12/2017 | |
|---|---|---|---|
| KR | 1796287 B1 * | 11/2017 | ......... A61F 13/0206 |
| WO | WO-1996/10972 A1 | 4/1996 | |
| WO | WO 2007/113597 A2 | 10/2007 | |
| WO | WO-2014/058532 A1 | 4/2014 | |
| WO | WO-2016/030047 A1 | 6/2015 | |

OTHER PUBLICATIONS

International Search Report and Written Opinion were mailed on Mar. 1, 2019 by the International Searching Authority for International Application No. PCT/EP2018/084744, filed on Dec. 13, 2018 and published as WO/2019/115686 on Jun. 20, 2019 (Applicant—Mölnlycke Health Care AB) (12 Pages).

* cited by examiner

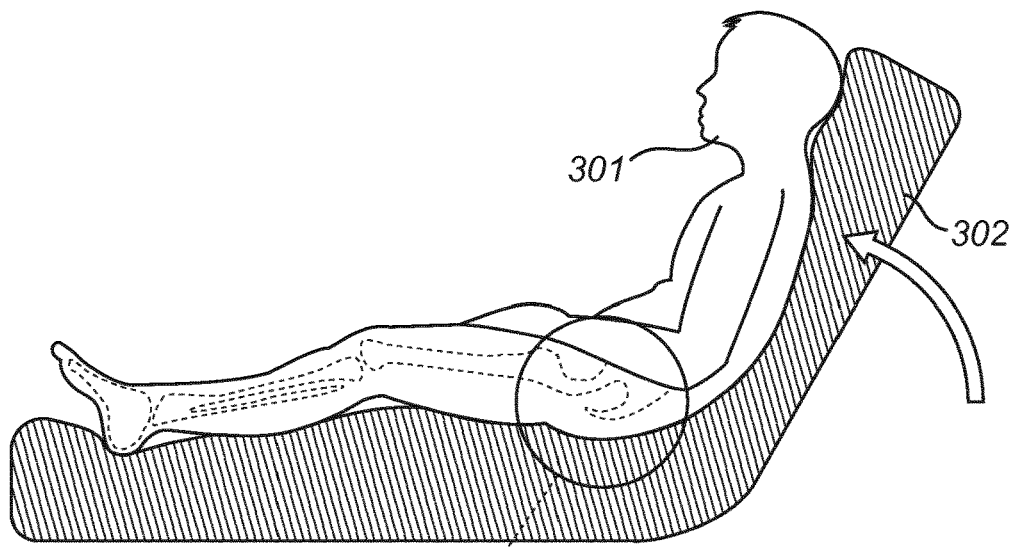
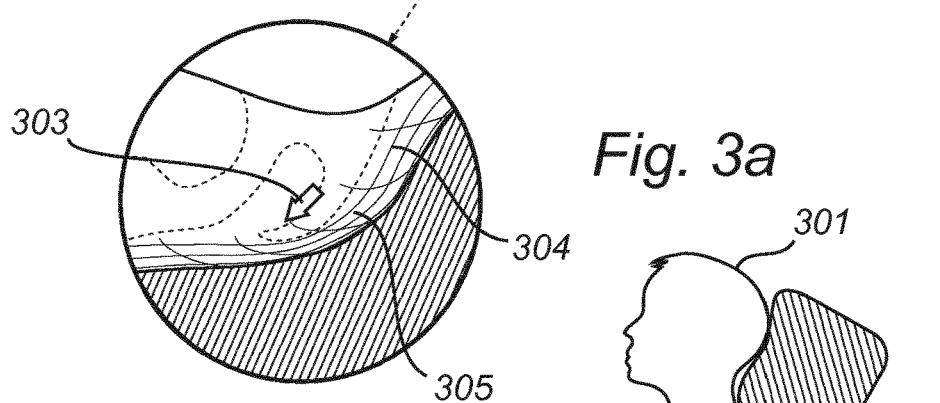
Fig. 3a
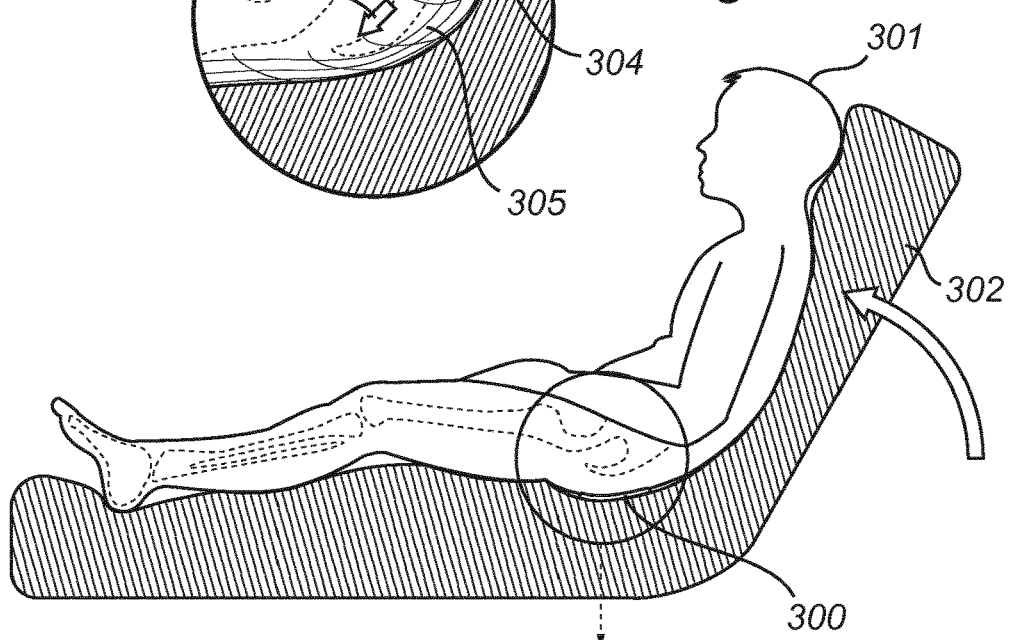
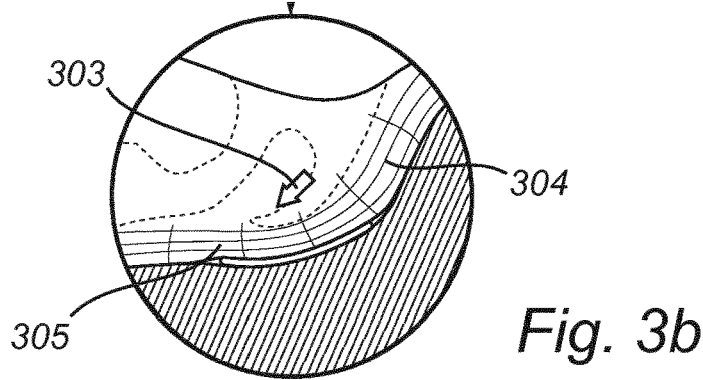
Fig. 3b

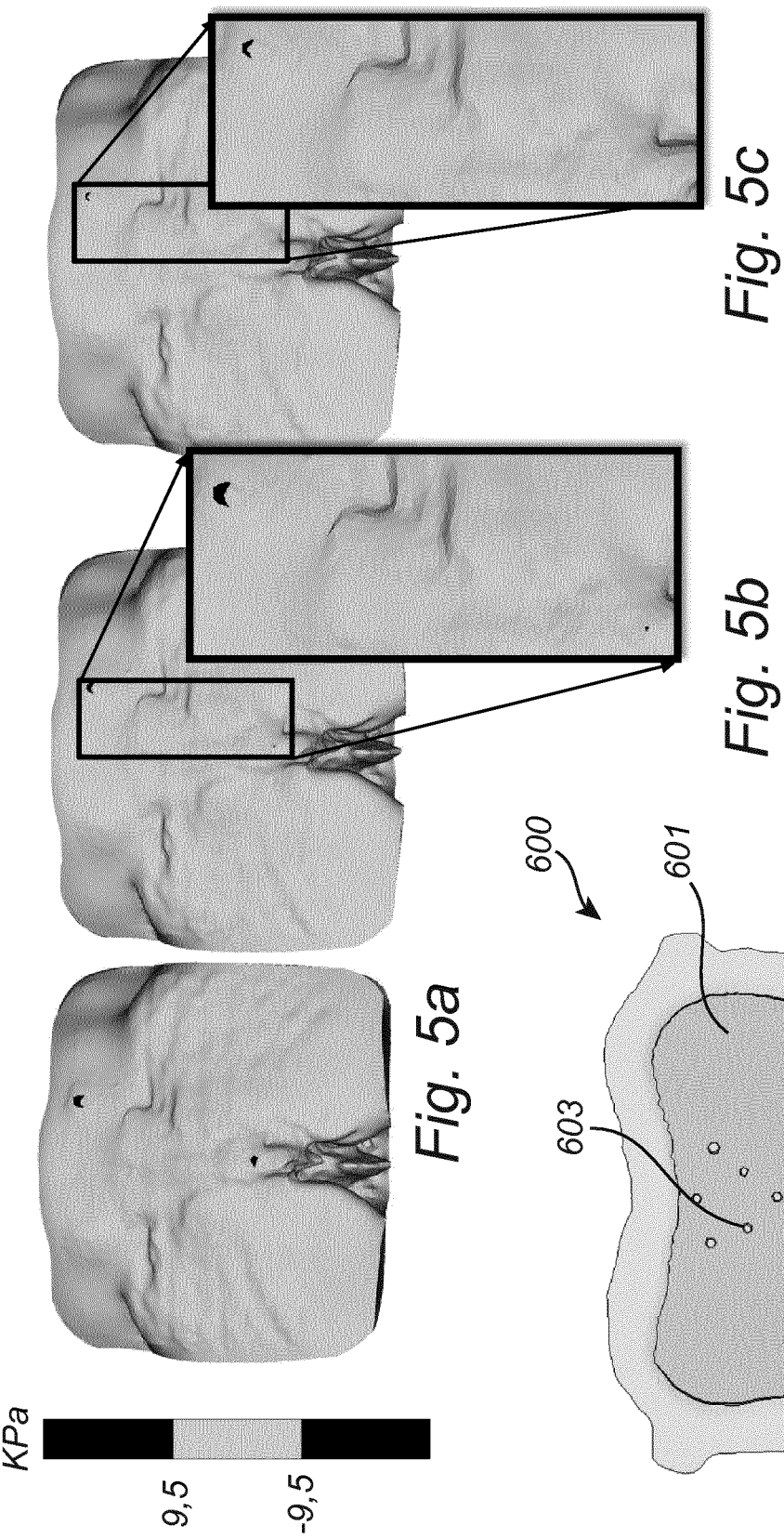
*Fig. 5a*  *Fig. 5b*  *Fig. 5c*
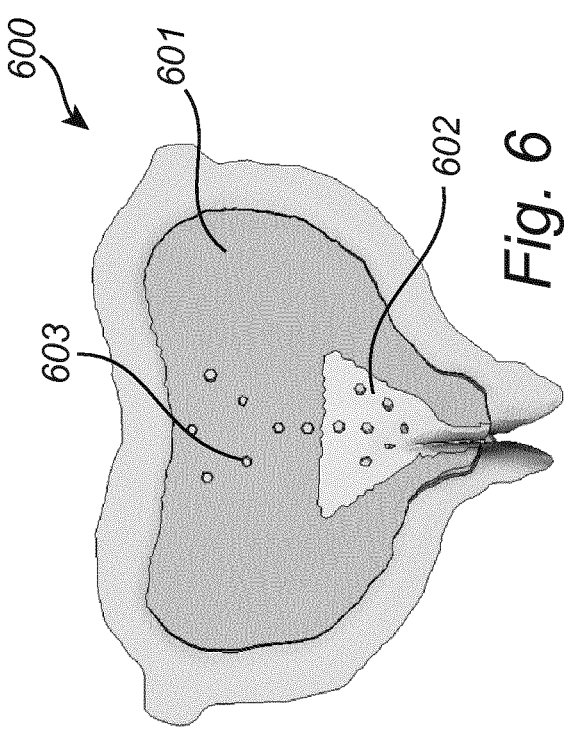
*Fig. 6*

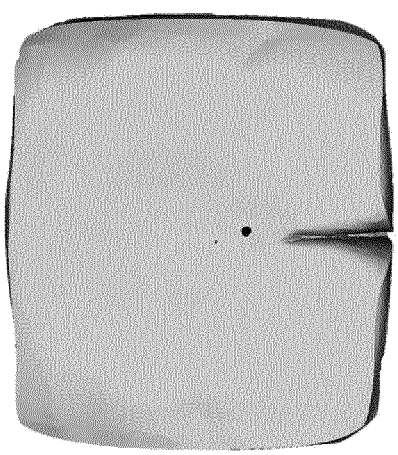
Fig. 7a
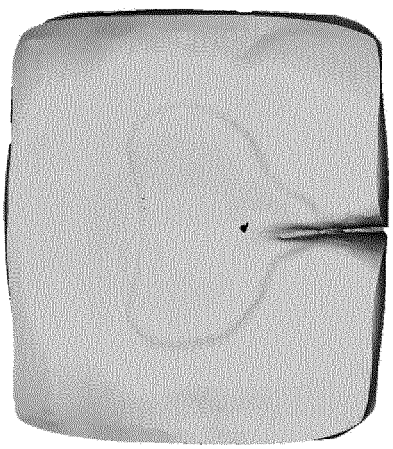
Fig. 7b
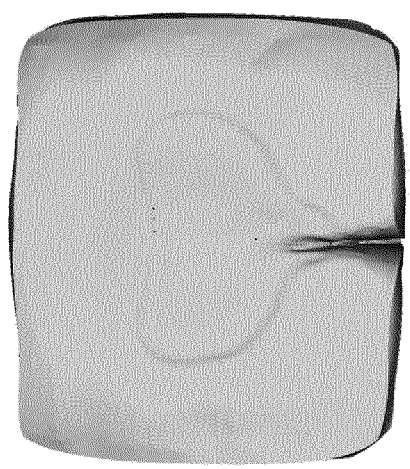
Fig. 7c

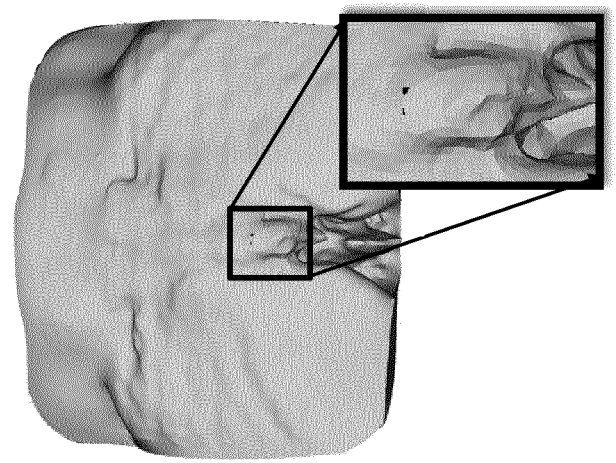
*Fig. 8c*
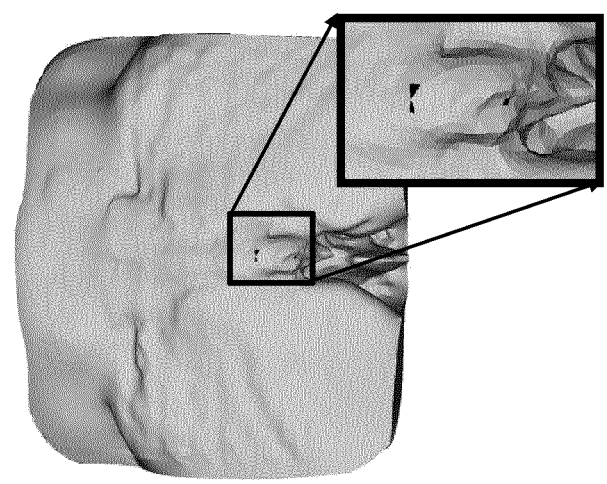
*Fig. 8b*
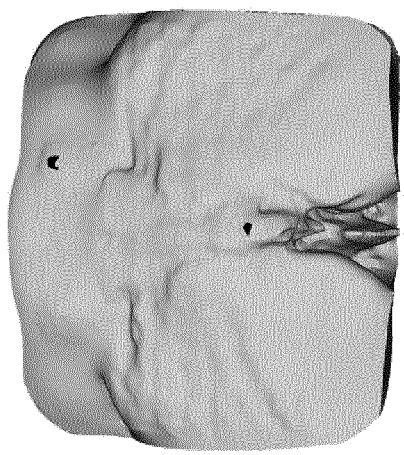
*Fig. 8a*
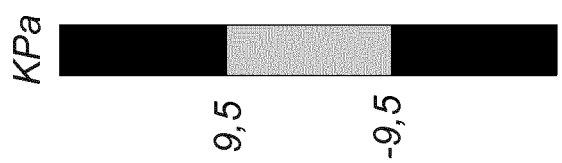

MEDICAL DRESSING

CROSS-REFERENCE TO RELATED APPLICATIONS

This application is a U.S. National Phase Application of International Application No. PCT/EP2018/084744, filed Dec. 13, 2018, which claims priority to European Application No. 17207756.2, filed Dec. 15, 2017.

TECHNICAL FIELD

The present invention relates to a medical dressing comprising a body contact layer with anisotropic stiffness properties. The dressing is suitable for the prevention of pressure ulcers.

BACKGROUND

A pressure ulcer is a localized injury to the skin and/or underlying tissue over a bony prominence that results from sustained pressure, often in combination with friction and shear. The major factors leading to pressure ulcers or pressure injuries are pressure, shear, friction and unfavourable microclimate. Other factors, intrinsic to patients, may also increase the likelihood of pressure ulcer development, e.g. poor perfusion, reduced sensation and inadequate nutrition. Pressure ulcers often arise among persons being bedridden for various reasons, such as for instance due to long term hospitalization or other causes of immobility. Pressure ulcers may also occur beneath medical devices, such as nasogastric tubes, ventilation masks and tracheostomy tubes, which are applied for diagnostic or therapeutic purposes. The rigid materials used in these devices may abraden the skin and create pressure on the soft tissues.

A pressure ulcer does not always start at the skin surface. What is observed at the skin is often only a small part of the sore, and this may mislead the patient or his/her caregiver to believe that there is only a minor problem.

Pressure ulcers often develop in soft tissue under the skin which covers bony areas of the body (so called "bony prominences"), for example the heels, ankles, the hips or the sacrum. Pressure and shear forces cause blood vessels to become squeezed between the skin surface and bone. Hence, muscles and tissue under the skin near the bone surface typically suffer the greatest damage. Accordingly, any pressure ulcer as apparent on the skin, regardless of how small, should be regarded as critical because of the probable damage below the skin surface.

A pressure ulcer can be classified into four categories: in the first category, the skin appears pink, reddened or discoloured, and may feel hard and warm to touch. In the second category, the skin breaks open and an ulcer that may look like a blister is formed. In this stage, the skin may be damaged beyond repair or may die. A category 3 pressure ulcer is an ulcer that extends into the tissue beneath the skin, forming a small crater. In category four, the pressure sore is very deep, reaching into the muscle and bone and causing extensive damage to deeper tissue and tendons. Serious complications, such as infection of the bone or blood can occur if the pressure ulcer progresses.

In a hospital or care facility, caregivers adhere to specific protocols to prevent the occurrence of pressure ulcers. One important part in the prevention regimen is regular inspection of the skin.

In some hospitals, caregivers apply wound dressings to areas at risk of developing pressure sores, for example in the sacrum, at the heels and under medical devices such as oxygen masks, and feeding, tracheostomy and nasogastric tubes. The dressings used are not primarily designed for prophylactic purposes.

Furthermore, when a dressing has been applied, the skin underneath the dressing must be regularly inspected, typically at least twice a day, to assess the skin status and ensure that there is no sign of damage. This requires the dressing to be peeled back to allow for assessment of the skin and any bony prominence covered. The dressing may need to be opened up and re-applied several times during the day. The adhesive capacity of dressing may thus be impaired.

Pressure ulcers are a global problem and the possibility to prevent these is desirable both to reduce human suffering but also to avoid unnecessary costs. The average cost for a category 3 or 4 pressure ulcer is from 75000 to 125000 US dollars per patient.

To summarize, there is a need to provide a dressing having an improved prophylactic effect; i.e. a dressing aimed at preventing a pressure ulcer from occurring in the first place and for preventing the progress of an already existing pressure ulcer. Furthermore, there is a need to provide for a proactive and cost-efficient means to relieve the burden for caregivers and staff dealing with pressure ulcers.

SUMMARY

According to at least one aspect of the invention, there is provided a medical dressing comprising a backing layer, a pad, and a body contact layer, wherein the pad is arranged between the backing layer and the body contact layer, and wherein the backing layer and the body contact layer extend beyond the periphery of the pad to define a border portion around the contour of the pad, wherein the body contact layer comprises an adhesive skin contact layer and an anisotropic layer having a first (x) direction and a second (y) direction perpendicular to the first (x) direction, wherein the anisotropic layer is stiffer in the second (y) direction than in first (x) direction.

The medical dressing is particularly useful for pressure ulcer prevention and/or pressure ulcer mitigation. The inventors have found that by incorporating a layer having anisotropic stiffness into the dressing, the formation of pressure ulcers may be prevented or reduced. This effect is particularly observed if the anisotropic layer is arranged in close proximity to the skin of a patient. In use, the dressing should be applied such that the second (y) direction of the anisotropic layer (and the dressing) correspond to the direction of which the patient is exposed to most shear forces.

For example, when the dressing is applied to the sacral region of a patient, the dressing is stiffer in the direction in which the patient slides in bed. This is normally along the length of the patient. On the other hand, the first (x) direction of the dressing is preferably more stretchable and pliable. This is beneficial since the first (x) direction of the dressing corresponds to the direction by which the patient, wearing such dressing, will be turned and re-positioned by nursing personnel.

A bedridden patient at risk of developing pressure ulcers must be turned and repositioned at regular intervals. It is therefore advantageous that the dressing conforms to this lateral movement and stays on the skin. Furthermore, stretchability in the first (x) direction is advantageous since it prevents the skin and underlying tissues from becoming "over constrained" which could otherwise be the case when the dressing is too stiff in both the first and the second directions.

In embodiments, the body contact layer further comprises a plastic film.

Hence, the body contact layer may comprise three different layers.

The integrity and rigidity of the body contact layer, and hence also of the border portion is thereby enhanced. This is beneficial since it facilitates skin inspection. A caregiver must regularly inspect the skin beneath the dressing, which requires the dressing to be detached and re-attached several times a day. If the border portion is too thin and "flimsy", wrinkles may form when the dressing is re-applied to the skin. This may reduce the adhesive capacity of the border (and the body contact layer), and hence also the wear time of the dressing.

A body contact layer comprising an anisotropic layer increases the rigidity of the border and prevents it from "rolling up" when the dressing is in use, as well preventing wrinkle formation when re-applied.

In exemplary embodiments, the plastic film is arranged between the anisotropic layer and the adhesive skin-facing layer.

In alternative embodiments, the anisotropic layer is arranged between the adhesive skin-facing layer and the plastic film.

Both embodiments are equally conceivable and benefit from same advantages of providing rigidity to a thin and "flimsy" border portion, and reducing shear and compression forces in the soft tissue beneath the dressing.

In embodiments, the anisotropic layer has a tensile force at 15% strain in the second (y) direction of at least 4 N, preferably at least 10 N, most preferably at least 15 N as measured by the tensile test described herein.

The prophylactic effect of the dressing is thereby improved, and the skin cells and underlying soft tissue cells are protected from becoming extensively damaged. The structural integrity of the dressing is enhanced, and the pressure and shear forces inflicted on a patient laying down on a hospital bed (e.g. a bedridden patient) are reduced. Stiffness in the direction of shear exposure protects the skin cells and deeper tissue layer cells from stretching, and thereby deforming.

In embodiments, the anisotropic layer has a tensile force at 15% strain in the second (y) direction that is at least 6 times higher, preferably at least 10 times higher than in the first (x) direction, as measured by the tensile test described herein.

Accordingly, the stay-on ability of the dressing on the skin is enhanced, and the skin and underlying tissue is prevented from becoming over constrained which could otherwise be the case if the dressing is too stiff in both the first (x) and the second (y) directions.

In embodiments, the anisotropic layer comprises a nonwoven.

This may be beneficial since many nonwoven materials can be manufactured with directional stiffness, e.g. by orienting the fibers in the longitudinal direction such that reinforcement will be provided in this direction. Also a nonwoven may improve the spreading of moisture entering the dressing leading to a better transport of moist into the dressing and away from the skin.

Also, in embodiments where the anisotropic layer is arranged between the plastic film layer and the adhesive skin-surface layer, the lamination process is improved since the adhesive layer adheres better to the nonwoven, and since any additional components of the dressing (pad etc.) are easier to apply.

In embodiments, the plastic film comprises polyurethane.

A polyurethane film is flexible and tear-resistant even at small thicknesses.

In embodiments, the skin-facing adhesive layer comprises a silicone gel.

A silicone gel based adhesive is skin-friendly, and easy to remove without causing trauma. It is sufficiently adherent to skin such that the dressing stays in place, and maintains its adherence with repeated removal and re-application.

In embodiments, the body contact layer comprises a plurality of apertures.

The apertures may extend through the entire body contact layer, or at least through the adhesive skin-facing layer. The apertures serve to improve the absorption of fluid into the pad without compromising the tight fit to the skin provided by the adhesive first layer.

The apertures may have a shape that enhances the anisotropic characteristics of the body contact layer; and hence also the dressing. Thus, in embodiments, the plurality of apertures are selected from a plurality of elongated cuts or elongated openings, such as elliptical holes, wherein each elongated cut or elongated opening has a length direction and a width direction, and wherein the length direction is the same as or parallel with the second (y) direction.

This arrangement of apertures increases the stretchability in the first (x) direction, but not in the second (y) direction. When the dressing and the patient are subject to stretching, e.g. due to turning of a patient, the elongated cuts or openings can extend in their width direction, which correspond to the first (x) direction of the dressing.

In order to further enhance the prophylactic effect of the dressing, the dressing may comprise a second anisotropic layer being stiffer in the second (y) direction than in the first (x) direction.

In embodiments, the second anisotropic layer has a tensile force at 15% strain in the second (y) direction that is at least 6 times higher, preferably at least 10 times higher than in the first (x) direction, as measured by the tensile test described herein.

The incorporation of two different anisotropic layers having directional stiffness in the second (y) direction yields a synergetic prophylactic effect, and the protection of soft tissue cells is further improved.

In exemplary embodiments, the dressing comprises at least one gripping tab; the gripping tab being coplanar with and projecting outwardly from the border portion of the dressing.

As mentioned, regular inspection of the skin is an important procedure in the hospital and caregiver routines for preventing pressure ulcers. The gripping tab facilitates inspection of the skin by guiding the caregiver to lift the dressing, inspect the skin underneath the dressing, and to thereafter re-apply the dressing onto the skin.

In another aspect, the invention relates to a dressing as described hereinbefore for use in the prevention and/or mitigation of pressure ulcers.

However, although the primary use of the invention is for prevention, such a dressing may also be used in the treatment of pressure ulcers or wounds.

Further features of, and advantages with, the present invention will become apparent when studying the appended claims and the following description. The skilled addressee realizes that different features of the present invention may be combined to create embodiments other than those described in the following, without departing from the scope of the present invention.

BRIEF DESCRIPTION OF THE DRAWINGS

FIG. 2b is a zoomed-in view of the body contact layer of the dressing illustrated in FIG. 2a.

FIG. 3 illustrates a bedridden patient exposed to pressure and shear forces when the head of the bed is tilted upwards when no dressing is used (3a), and when a dressing of the invention has been applied to the sacrum region of the patient (3b).

FIG. 5 illustrates the Von Mises stress distribution at the muscle arising from compression in a Finite element (FE) model simulation, when no dressing is used (FIG. 5a), a foam pad (FIG. 5b) and dressing according to exemplary embodiments of the present invention (FIG. 5c).

FIG. 6 illustrates a simulated gel based dressing with a central pad zone comprising apertures and a lower pad region with a lower gel compressive strength.

FIG. 7 illustrates the mean pressure (hydrostatic stress) distribution at the skin arising from compression in a Finite element (FE) model simulation, when no dressing is used (FIG. 7a), a dressing comprising an anisotropic layer in the pad (FIG. 7b) and a dressing according to the present invention comprising an anisotropic layer in close proximity of the skin (FIG. 7c).

FIG. 8 illustrates the Von Mises stress distribution at the muscle arising from compression in a Finite element (FE) model simulation, when no dressing is used (FIG. 8a), a dressing comprising an anisotropic layer in the pad (FIG. 8b) and a dressing according to the present invention comprising an anisotropic layer in close proximity of the skin (FIG. 8c).

DETAILED DESCRIPTION

The present invention will now be described more fully hereinafter with reference to the accompanying drawings, in which currently preferred embodiments of the present invention are shown. The present invention may, however, be embodied in many different forms and should not be construed as limited to the embodiments set forth herein; rather, these embodiments are provided for thoroughness and completeness, and fully convey the scope of the present invention to the skilled person.

FIG. 1 conceptually illustrates how pressure, shear and friction contribute to pressure ulcer development.

Figure 1A:
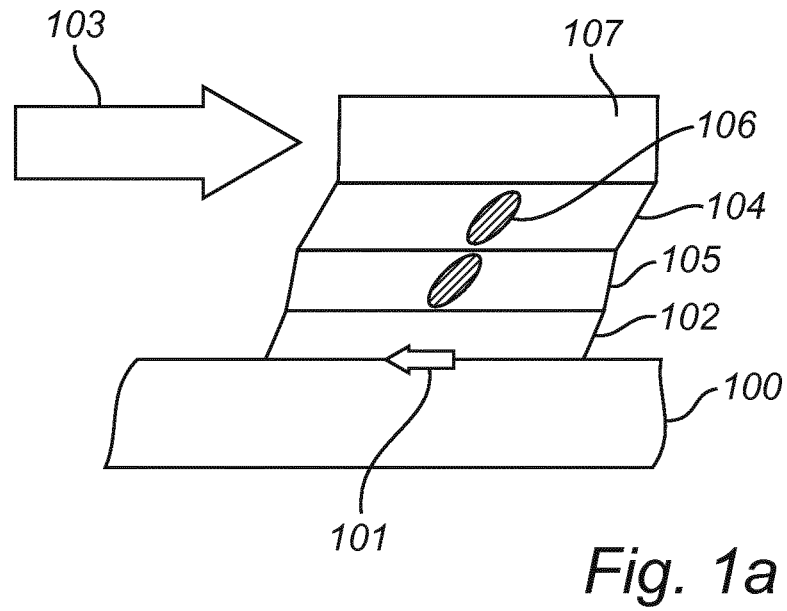
FIGS. 1a and 1b schematically illustrate how pressure, shear and friction contribute to the development of pressure ulcers.

Referring to FIG. 1a, when a patient in contact with a support surface 100 moves, friction 101 between the skin 102 and the support surface 100 tends to hold the skin 102 in place and a shear force 103 occurs that displaces and deforms the deeper tissues (muscle 104 and adipose tissue 105). The deeper tissue layers 105 and 104 are subject to the worst effect of shear since these layers, in closer proximity to the bone 107, cannot move in a manner like the skin layer 102 does. Instead these layer are stretched but still "stuck". Furthermore, blood vessels 106 are distorted and compressed. Compression of blood vessels 106 by pressure and/or shear may reduce the blood flow to tissues. This may result in tissue hypoxia, build-up of metabolic waste products and, eventually, tissue damage.

Figure 1B:
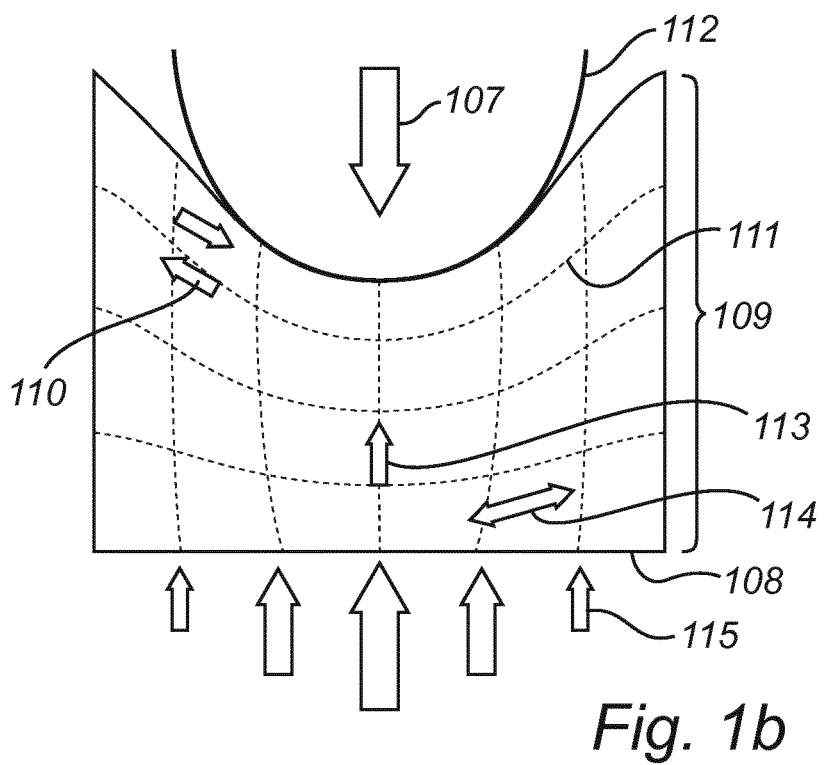

Referring to FIG. 1b, when a force 107 is applied perpendicular to the surface of the skin, pressure is exerted onto the skin 108 and subcutaneous tissues 109. Pressure 107 compresses the tissues 109 and may distort or deform the skin and the soft tissues (e.g. subcutaneous fat and muscle). Shear 110 may also occur in and between layers 111 of deeper tissues as a result of tissue deformation caused by pressure over a bony prominence 112. Muscle is particularly prone to damage by shear. Compression stresses 113 occur in the axis perpendicular to the direction of the muscle fibers, and tensile stresses 114 occur when the tissue is stretched and deformed along the fiber direction. The arrows 115 represent surface pressure. Deformation of soft tissues is greater when pressure is applied over a bony prominence 112. Damage thus often occur initially in the soft tissue, i.e. at the muscle/bone interface, and skin breakdown and pressure sore formation occurs later in the process. Hence, when assessing a pressure sore, the full extent of the damage may not be clear or visible.

FIG. 2 illustrates a dressing according to an exemplary embodiment of the present invention. The dressing 200 comprises a backing layer 201, a pad 202, and a body contact layer 203, wherein the pad 202 is arranged between the backing layer 201 and the body contact layer 203 and wherein the backing layer 201 and the body contact layer 203 extend beyond the periphery of the pad 202 to define a border portion 204 around the contour of the pad, wherein the body contact layer 203 comprises an adhesive skin contact layer 207 and an anisotropic layer 205 having a first (x) direction and a second (y) direction perpendicular to the first (x) direction, wherein the anisotropic layer 205 is stiffer in the second (y) direction than in the first (x) direction.

The first (x) direction of the anisotropic layer 205 may also be referred to as the lateral (x) direction, and the second (y) direction may also be referred to as the longitudinal (y) direction.

As used herein, the term "stiffer" means that the anisotropic layer has a higher tensile force at 15% strain in the second (y) direction than in the first (x) direction, as measured according to the tensile test described hereinafter.

As used herein, the term "anisotropic layer" means a layer that has anisotropic stiffness properties; i.e. the stiffness or stretchability is different in the lateral (x) and second (y) directions of the layer. In the present invention, the "anisotropic layer" is stiffer in the second (y) direction and more stretchable in the first (x) direction.

As used herein, the term "body contact layer" means the layer that is in contact with the skin of a wearer. In the field of medical dressings, in particular, wound dressings, an adhesive film or layer for adhering to the patient is often referred to as a wound contact layer. The present invention is primarily intended for pressure ulcer prevention, i.e. for use on a human body area which is not necessarily in need of wound treatment. Therefore, in this application the adhesive film or layer will be referred to as a body contact layer. However, it should be understood that although the primary use of the invention is pressure ulcer prevention, if nursing personnel decides to use it as a wound dressing, the body contact layer could be applied onto a wound or a scar.

In exemplary embodiments, the body contact layer 203 comprises a plastic film 206.

Figure 2A:
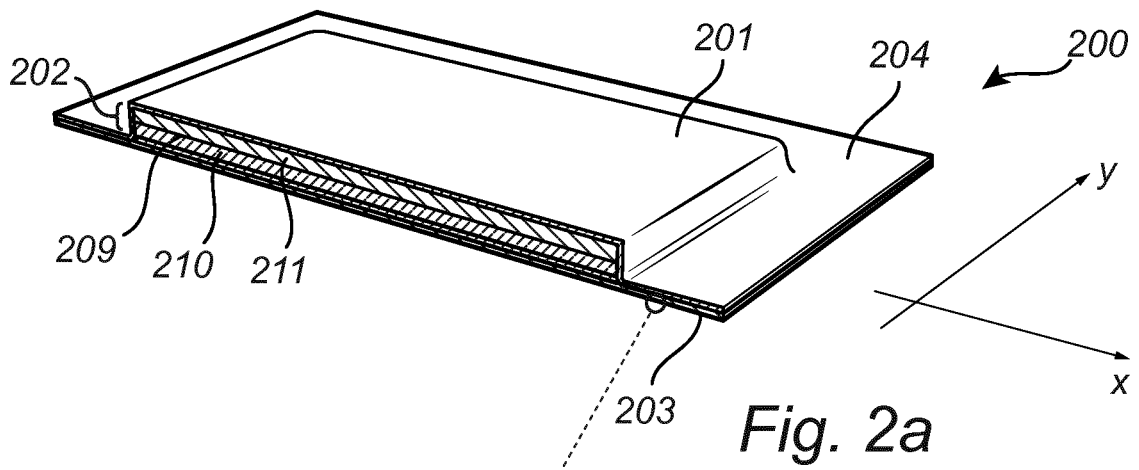
FIG. 2a is a cross-sectional view according to one exemplary embodiment of the present invention.
Figure 2B:
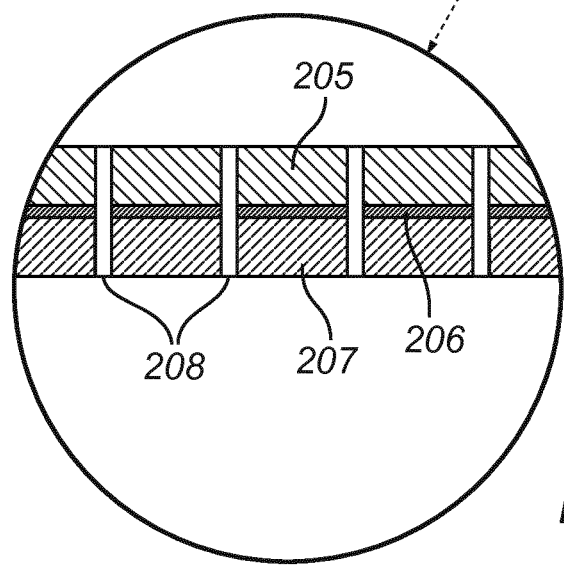
Figure 2C:
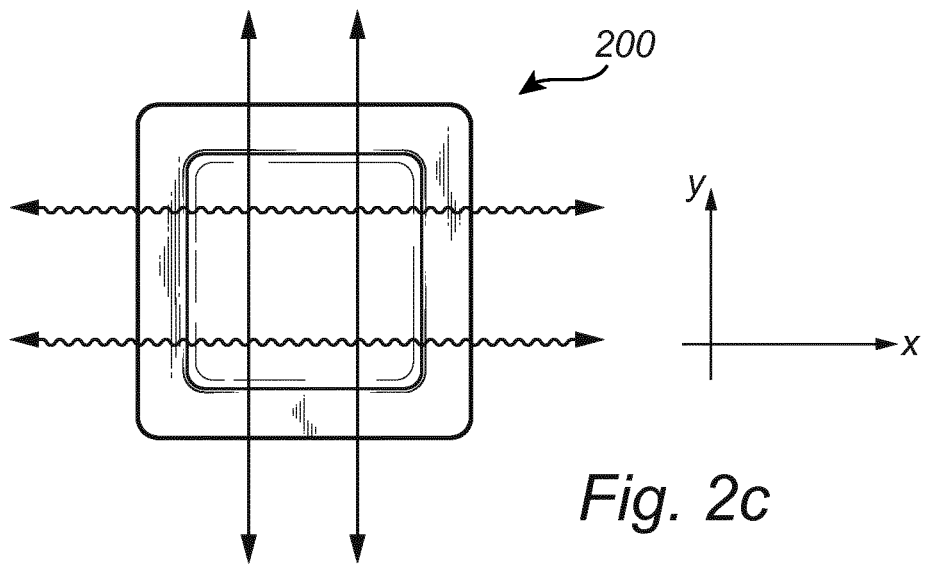
FIG. 2c illustrates the anisotropic properties of a dressing according to the present invention.

As illustrated in FIG. 2b, the plastic film 206 is arranged between the anisotropic layer 205 and the adhesive skin contact layer 207.

It is however equally conceivable that the anisotropic layer 205 is arranged between the plastic film 206 and the adhesive skin contact layer 207.

In the exemplary construction illustrated in FIG. 2b, the adhesive skin contact layer 207 is arranged to contact the skin of a wearer, the plastic film 206 is arranged on top of the second layer 206, and the anisotropic layer 205 is arranged on top of the plastic film 206.

The anisotropic layer 205 affects the stiffness of the entire dressing. As illustrated by the arrows in FIG. 2c, the dressing 200 is stiffer in the second (y) direction and more stretchable in the first (x) direction.

Suitably, the anisotropic layer 205 has a tensile force at 15% strain in the second (y) direction of at least 4 N, preferably at least 10, more preferably at least 15 N, as measured by the tensile test described herein.

In exemplary embodiments, the tensile force at 15% strain in the second (y) direction is at least 6 times higher, preferably at least 10 times higher than in the first (x) direction, as measured by the tensile test described herein.

The advantages of providing directional stiffness in the second (y) direction will be described more fully with reference to FIG. 3 further on in the specification.

The anisotropic layer 205 may be selected from a variety of materials such as nonwovens, films, textile materials, polymeric net materials as long as they exhibit the desired anisotropic stiffness properties. The anisotropic layer 205 may comprise a plurality of reinforcement fibres or filaments extending in the longitudinal direction. The reinforcement fibres or filaments provide the layer with high tensile force in the longitudinal (y) direction. Films or nets made of e.g. polyethylene, polypropylene, polyester, polyurethane or silicone can be used as long as these materials have sufficient strength in the longitudinal direction (y) and sufficient anisotropic properties.

In embodiments, the anisotropic layer 205 comprises a nonwoven. Suitable nonwovens for use as the anisotropic layer are meltblown, spunbond, spunlaced or carded nonwoven webs.

In exemplary embodiments, the anisotropic layer is an oriented fibrous nonwoven layer having more than 50% of the fibres oriented in the longitudinal (y) direction. In this manner, the fibres oriented in the longitudinal (y) direction will provide reinforcement in this direction.

Examples of suitable polymers for use in the nonwoven are polyethylene, polyesters, polypropylene and other polyolefin homopolymers and copolymers. For example, nonwoven webs comprising thermoplastic fibres of polypropylene and polyethylene fibres or mixtures thereof may be used. The webs may have a high content of thermoplastic fibres and contain at least 50%, e.g. at least 70% thermoplastic fibres. The nonwoven may be a mixture of polyethylene and viscose, e.g. in a 70:30 ratio. Natural fibres, for example cotton may also be used as long as they provide the desired properties. The basis weight of the nonwoven may be in the range of from 10 to 80 g/m2, e.g. of from 13 to 50 g/m2. The anisotropic layer may also be a spunbond-meltblown or spunbond-meltblown-spunbond (SMS) web.

The plastic film 206 may be a breathable polyolefin based film comprising e.g. polyethylene, polyamide, polyester polyurethane or silicone.

In exemplary embodiments, the plastic film 206 comprises polyurethane. Suitably, the plastic film 206 is a thin polyurethane film. For example, the film may be a polyurethane film having a thickness from 15 and 100 µm, e.g. from 20 to 80 µm, preferably from 20 to 60 µm.

In embodiments, the adhesive skin contact layer 207 comprises a silicone gel. The silicone gel is skin-friendly, and easy to remove without causing trauma. It is sufficiently adherent to skin such that the dressing stays in place, and maintains its adherence with repeated removal and re-application.

Examples of suitable silicone gels include the two component RTV systems, such as Q72218 (Dow Corning), and SilGel 612 (Wacker Chemie AG) mentioned herein, as well as NuSil silicone elastomers. In embodiments of the invention the adhesive may comprise a soft silicone gel having a softness (penetration) of from 8 to 22 mm, e.g. from 12 to 17 mm, as measured by a method based on ASTM D 937 and DIN 51580, the method being described in European Patent Application No 14194054.4. The thickness of the adhesive layer is preferably at least 20 µm.

The body contact layer 203 may be a laminate. Lamination of the different layers in the body contact layer may be made in any suitable manner, such as by adhesive, stitching, extrusion coating, ultrasonic welding or thermowelding. Any commonly used type of adhesive may be used, such as curable adhesives, solvent based adhesives or thermoplastic adhesives.

In exemplary embodiments, the body contact layer 203 comprises a plurality of apertures 208.

The apertures 208 may extend at least through the adhesive skin facing layer 207.

In the case where the body contact layer 203 comprises more than two layers or films, the apertures may extend through at least two of the layers of the body contact layer 203.

In embodiments, as illustrated in FIG. 2b, the apertures 208 extend through all the layers of the body contact layer 203.

The apertures 208 improve the absorption of body fluids into the dressing without compromising the adhesiveness to the skin area.

In embodiments, the plurality of apertures are selected from a plurality of elongated cuts or elongated openings, such as elliptical holes, wherein each elongated cut or elongated opening has a length direction and a width direction, and wherein the length direction is the same as or parallel with the second direction (y).

This way, the anisotropic characteristics of the body contact layer are further enhanced. When the skin is stretched, for example when a bedridden patient is turned, the elongated cuts or openings are stretched and extended in their width direction, which correspond to the first (x) direction of the dressing. However, the body contact layer still remains its stiffness in the longitudinal direction (y).

Figure 2D:
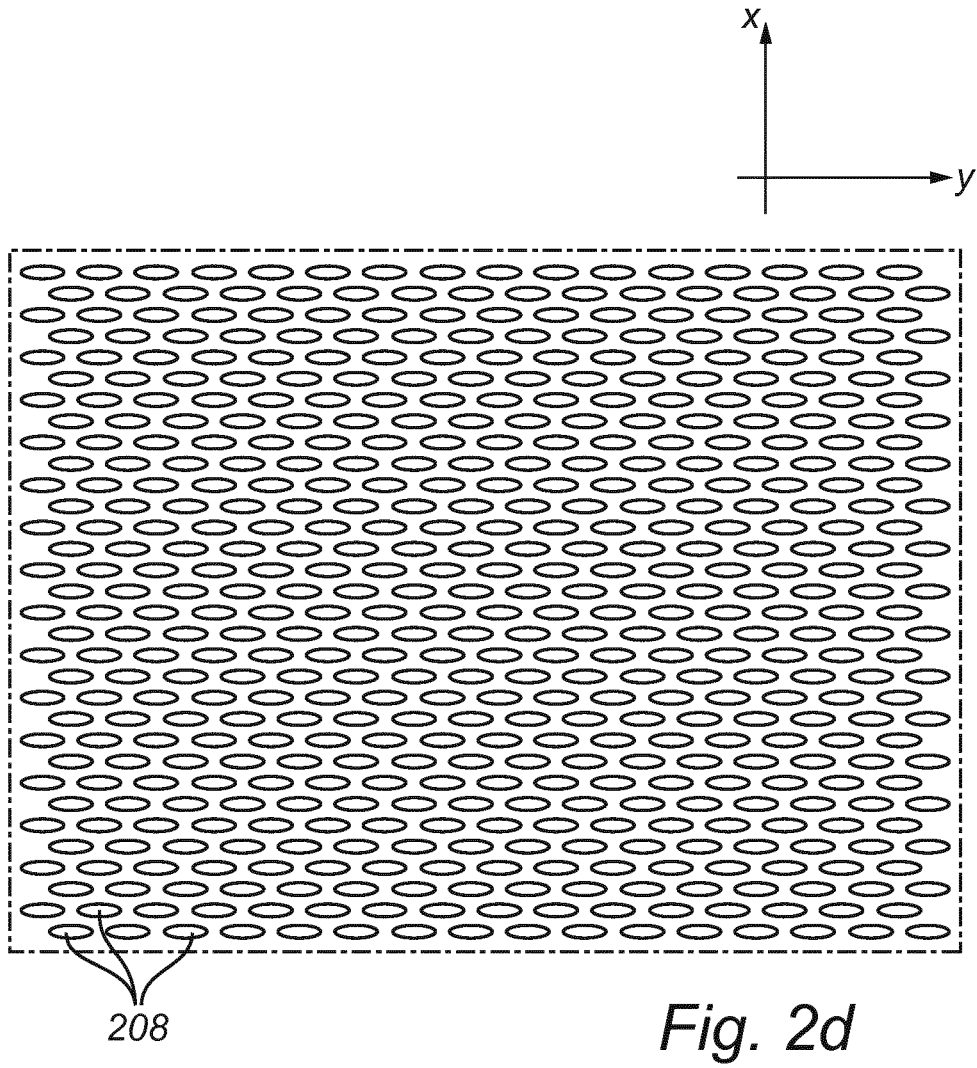
FIG. 2d illustrates an anisotropic body contact layer provided with elliptical apertures according to an exemplary embodiment of the invention.
Figure 2E:
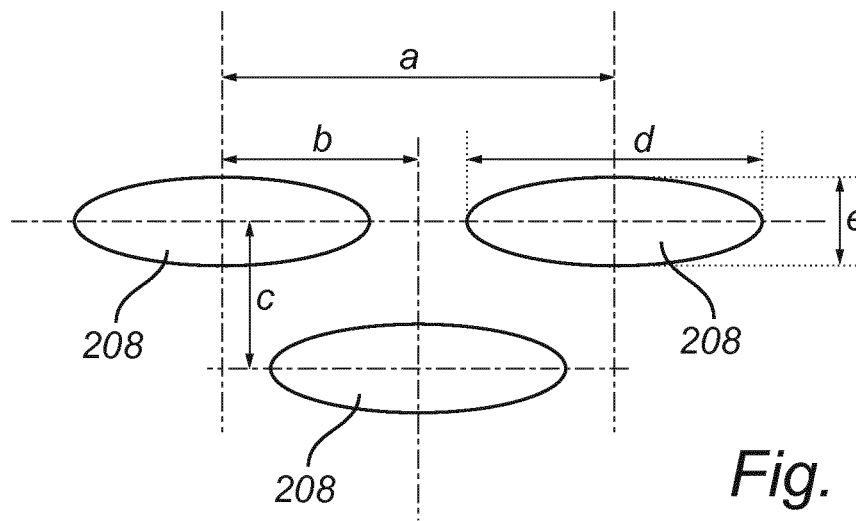
FIG. 2e is a zoomed in view of the body contact layer in FIG. 2d.

FIGS. 2d and 2e illustrate an example of how the apertures 208 in the body contact layer 203 may be distributed in the body contact layer.

FIG. 2d illustrates a pattern of apertures 208 in the form of elongated openings, such as elliptical openings. The apertures 208 are arranged in parallel rows extending in the longitudinal (y) direction, which is also the length direction of each individual aperture 208 in a row. When viewing the pattern along the lateral (x) direction, every second row is longitudinally offset (suitably by half an aperture length). The apertures 208 may suitably cover 10-40% of the area of the body contact layer.

FIG. 2e schematically (not true to scale) illustrates exemplary dimensions of the apertures 208. The apertures may, for instance, have a length l and a width w, wherein 1.5w≤l≤10w, suitably 1.5w≤l≤6w. A suitable width w may be in the interval 0.5 mm-3 mm. The length l and width w may be based, for instance, on the desired absorption capability and/or adhesiveness of the medical dressing. In FIG. 2e, the width is denoted e, and the length is denoted d. The radius r of the curved ends of the apertures 208 may be in the interval w/12-w/2. The smallest space d between apertures may be at least 0.75 mm. As illustrated in FIG. 2e, that smallest space d is along a diagonal or oblique extension (relative to the longitudingal (y) and lateral (x) directions. In each row, the separating distance a between two neighbouring elongated cuts or elongated openings, as measured centre-to-centre may, for instance, be 1.5-16 mm, or (related to the length l of the apertures) for instance 1.1l-2l. The length l may, for instance, be 0.75-15 mm. Neighbouring rows may suitably be separated from each other, as measured centre-to-centre, by a distance c of, for instance, 0.9-4 mm, or (related to the width w of the apertures) for instance 1.3w-1.8w. The width w may, for instance, be 0.5-3 mm. Furthermore, the apertures of neighbouring rows may be offset relative to each other by a distance b of, for instance, a/2.

In order to further enhance the prophylactic effect of the dressing, the dressing may comprise a second anisotropic layer being stiffer in the second (y) direction than in the first (x) direction.

The incorporation of two different anisotropic layers having directional stiffness in the second (y) direction yields a synergetic prophylactic effect, and the protection of soft tissue cells is further improved.

As illustrated in FIG. 2, the second anisotropic layer 209 may be arranged in the pad 202 of the dressing. The pad 202 may comprise one or more pad-forming layers.

In embodiments, the second anisotropic layer 209 has a tensile force at 15% strain in the second (y) direction that is at least 6 times higher, preferably at least 10 times higher than in the first (x) direction, as measured by the tensile test described herein.

The second anisotropic layer 209 may have a tensile force at 15% strain in the second (y) direction of at least 10 N, preferably at least 15 N, as measured by the tensile test described herein.

Accordingly, by controlling the directional stiffness of two different layers of the dressing, a synergetic effect is obtained. The anisotropic properties of the entire dressing is improved which has the effect that the skin cells and deeper tissue layer cells are protected from shear and compression resulting from long term exposure to pressure and sustained load. Thereby, the risk of developing pressure ulcers is minimized.

The pad may be comprised of the second anisotropic layer 209 only, or may comprise one or more layers.

For example, the pad may comprise a material that yields a pressure-relieving effect, e.g. a foam or a gel. This layer is denoted 210 in FIG. 2b.

In embodiments the pad comprises a superabsorbent material e.g. superabsorbent polymers (SAP) or superabsorbent fibers (SAF).

In embodiments, the pad comprises a first superabsorbent layer 211, a second anisotropic layer 209 and a third pressure relieving layer 210, wherein the second anisotropic layer 209 is arranged between the first superabsorbent layer 211 and the third pressure relieving layer 210.

If the second anisotropic layer 209 is a nonwoven, it may also serve as a liquid acquisition layer.

This pad construction is beneficial from a microclimate point of view. Moisture absorbed into the dressing is quickly transported away from the layer in closest contact with the skin (the third layer 210) to the first superabsorbent layer 211. Also, heat energy generated may be wicked away from the skin. Since heat increases the metabolism of the already stressed cells under pressure and shear, this could otherwise add to the deterioration of skin cells. The layered pad construction prevents accumulation of body liquids close to the skin.

The effect of a medical dressing exhibiting anisotropic stretching properties may be explained with reference to FIG. 3.

FIG. 3 illustrates a patient 301 positioned in an adjustable bed 302, where the head of the bed has been elevated and the patient 301 has been placed in a more upright condition. When no dressing is used (FIG. 3a), the patient 301 is subject to pressure compressing the tissue, and to shear forces 303 distorting or deforming the soft tissue layers 304. The individual tissue cells 305 are thus subject to both pressure and compression, and also to shear forces 303 that arise from the patient 301 sliding in bed 302. This has a negative impact on the soft tissue, and the tissue cells 305 are more prone to deformation, which ultimately may lead to the formation of a pressure ulcer.

In FIG. 3b, a dressing 300 according to the present invention has been applied to the sacrum region of the patient 301 such that the stiff, second direction (y) corresponds to the direction of which the tissue is exposed to most shear and stretch (i.e. the sliding direction of a patient). When a dressing is applied to the sacrum region, the pressure forces are reduced by the dressing 300 and distributed over a larger area. This leads to pressure re-distribution and reduced magnitude of critical forces on the skin and underlying tissue. The shear forces 303 are reduced by the dressing 300 since the dressing is stiff in the direction in which the patient 301 slides in bed 302. Therefore, the stiff dressing 300 "locks" the skin and underlying tissues such that they do not stretch excessively in the region where the dressing 300 is applied. The fact that the dressing is flexible in the first direction (x) is advantageous since it prevents the tissues from becoming "over constrained". Instead, the sacral buttocks can spread gently and naturally.

The individual tissue cells 305 in the sacral region of the patient 301 are therefore maintained relatively intact. The stretching of the skin may still occur at skin areas outside the dressing (which areas are at less risk for pressure ulcer formation caused by deformation, pressure and shear). This way, pressure forces, shear forces and the stress and stretch on skin cells and the underlying tissue cells are minimized.

In exemplary embodiments, the dressing comprises at least one gripping tab; the gripping tab being coplanar with and projecting outwardly from the border portion of the dressing.

Figure 4:
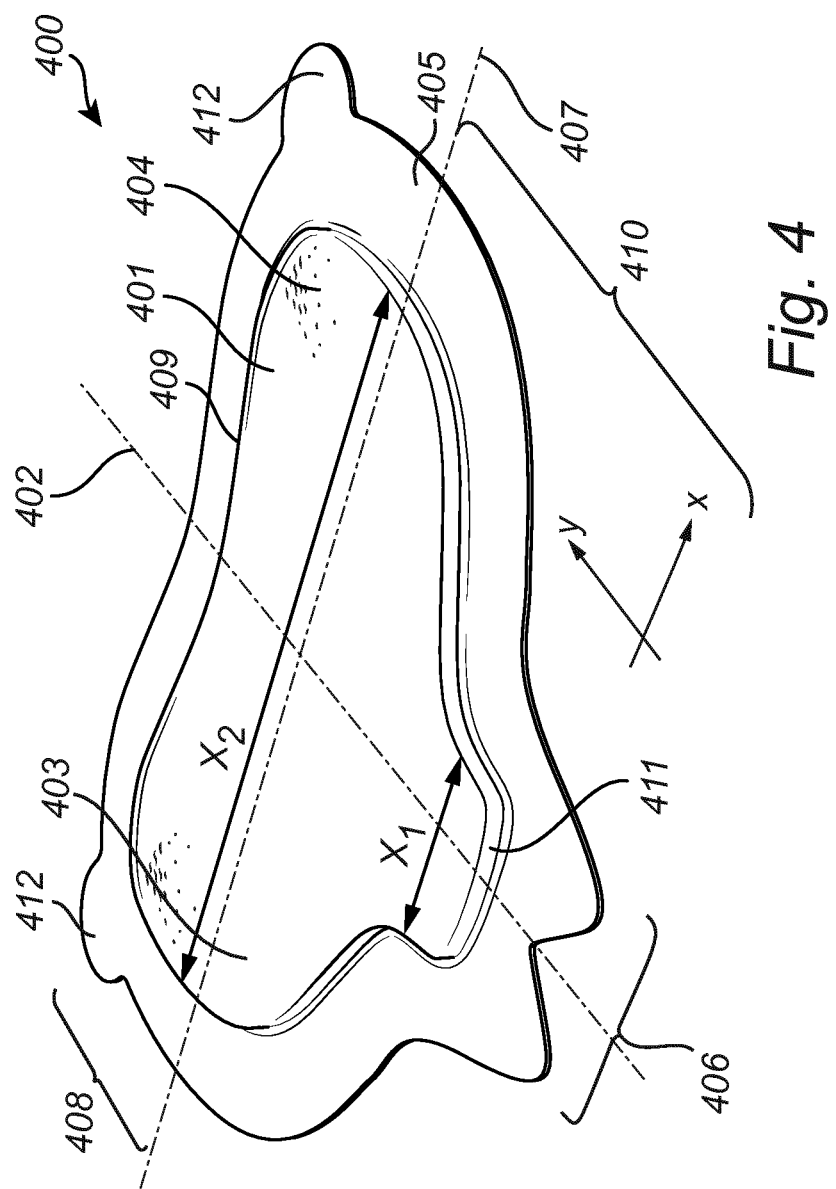
FIG. 4 illustrates an exemplary embodiment of the dressing according to the invention.

A dressing comprising two gripping tabs, and with a shape particularly suitable for application to the sacrum of a patient is illustrated in FIG. 4.

The medical dressing 400 illustrated in FIG. 4 has a lateral (x) extension and a longitudinal (y) extension; the pad 401 being symmetric about a longitudinal center line 402 and the dressing comprising a first lobed portion 403 on one side of the longitudinal center line 402 and a second lobed portion 404 on the other side of the longitudinal center line 402.

The anisotropic layer of the body contact layer (and the second anisotropic layer of the pad, if present) is (are) arranged such that the first direction (x) of the anisotropic layer corresponds to the lateral (x) extension of the dressing 400, and the second direction (y) of the anisotropic layer corresponds to the longitudinal extension of the dressing 400. Hence, the entire dressing is stiffer in the second (y) direction than in the first (x) direction.

The border portion 405 may be substantially heart shaped such that the first 403 and second 404 lobed portions form part of the lobed upper sides of a heart shape. Suitably, the first and second lobed portions are separated by a forked portion 406 which replaces the pointed lower part of a heart shape. The forked portion 406 comprises a protrusion on either side of an interstice located coaxially with the longitudinal center line.

The shape of the medical dressing 400 is adapted to fit to the sacral region of a human body. The forked portion 406 allows for an improved stay-on ability in the gluteal cleft region. It is important that the dressing remains adhered in this region since otherwise body fluids (for example as a result of incontinence) may enter into the dressing and impair the adhesion to the skin.

The coccyx is an area exposed to a large amount of pressure and shear. It is therefore important to protect this part of the body, and the dressing suitably has a shape that allows for such protection.

Hence, the pad 401 may be divided by a lateral center line 407 into an upper pad region 408 having an upper lateral edge 409 and a lower pad region 410 having a lower lateral edge 411. The width, x1, of the lower lateral edge 411 is between 10 and 40% of the maximum width, x2, of the pad 401 in the first (x) direction.

The maximum width, x2, of the pad of the dressing 400 is typically in the range of from 12 to 30 cm, e.g. from 15-20 cm. The width, x1, of the lower lateral edge may be in the range of from 1 to 7 cm, e.g. from 2 to 4 cm, depending on the size of the dressing.

The gripping tab(s) 412 guides the caregiver to lift the dressing, inspect the skin underneath the dressing, and to thereafter re-apply the dressing onto the skin (in case the skin looks ok). Since the inspection of the skin typically takes place where the patient is lying on the side in the bed, it is beneficial to have at least two gripping tabs such that the caregiver can lift the dressing regardless of which side the patient lies. In FIG. 6, the gripping tab 412 is coplanar with and projects outwardly from the border portion of one of the lobed portions 403 and 404.

In exemplary embodiments, the friction coefficient of the backing layer is between 0.4 and 1 as measured by the standard test method ASTM D 1894-14.

The friction coefficient is preferably low such that the friction between the dressing and the bed sheet is reduced when a patient slides in bed. Reducing friction is an important aspect, since friction is the source of shear. The backing layer acts as a "sliding layer" and prevents the translation of friction into harmful shear forces.

The backing layer may be a thin film, sheet or membrane that is vapour permeable and waterproof. Examples of suitable materials for the backing layer include, but are not limited to polyurethane, polyethylene or polyamide films, silicone films, polyester based nonwoven materials, and laminates of polyester-based nonwoven materials and polyurethane films. Suitably, the backing layer is a polyurethane film having a thickness of from 5 to 40 μm, e.g. from 15 to 25 μm.

In embodiments, the backing layer comprises a functional enhancement print, wherein the functional enhancement print is asymmetric in the lateral (x) and longitudinal directions (y) in a non-stretched state.

The printed backing layer visually communicates to the user the differences in functionality of the dressing. It also aids in guiding the user to select a dressing suitable for prevention purposes, and to distinguish it from a dressing specifically directed towards treatment of wounds.

For example, the functional enhancement print may be a continuous print selected from a lattice of ellipses, rectangles and lines intersecting as crosses.

In another aspect, the invention relates to a dressing as described hereinbefore for use in the prevention of pressure ulcers.

However, although the primary use of the invention is for prevention, such a dressing may also be used in the treatment of pressure ulcers or wounds, especially low exuding wounds. A prophylactic dressing needs to be able to handle low exuding wounds and body fluids such as sweat, small amounts of blood, and pus.

Examples

Tensile Force (Reference: ASTM D882-12)
  Apparatus: Tensile tester for e.g. MTS insight
  Tensile tester connected to a computer
  Crosshead speed: 50 mm/min
  Grip separation: 100 mm
  Sample preparation: Test specimens are punched from the material. The width of the specimens is 25 mm and the length at least 50 mm longer than the grip separation if possible. It is of importance that the edges of the specimens are even and without break notches. The specimens are conditioned for at least 24 h in 50 percent RH plus or minus 5 percent RH and 23 degrees centigrade plus or minus 2 degrees centigrade before testing.
  Procedure: The tensile tester is calibrated according to the apparatus instructions and set to zero. The sample is then mounted in the clamps and slack and pre-tension should be minimized. The tensile tester is started and the sample is elongated until break or until reaching 100% elongation, the tensile force (load) versus elongation is recorded. Measurements resulting from premature failures (i.e. the sample breaks at the clamp, or is damaged during preparation) are ignored if possible.

The following results are expressed by the tensile tester/computer:
  Strain [%], extension/gage length
  Load at specific strain (e.g. at 15% strain)

Figure 9A:
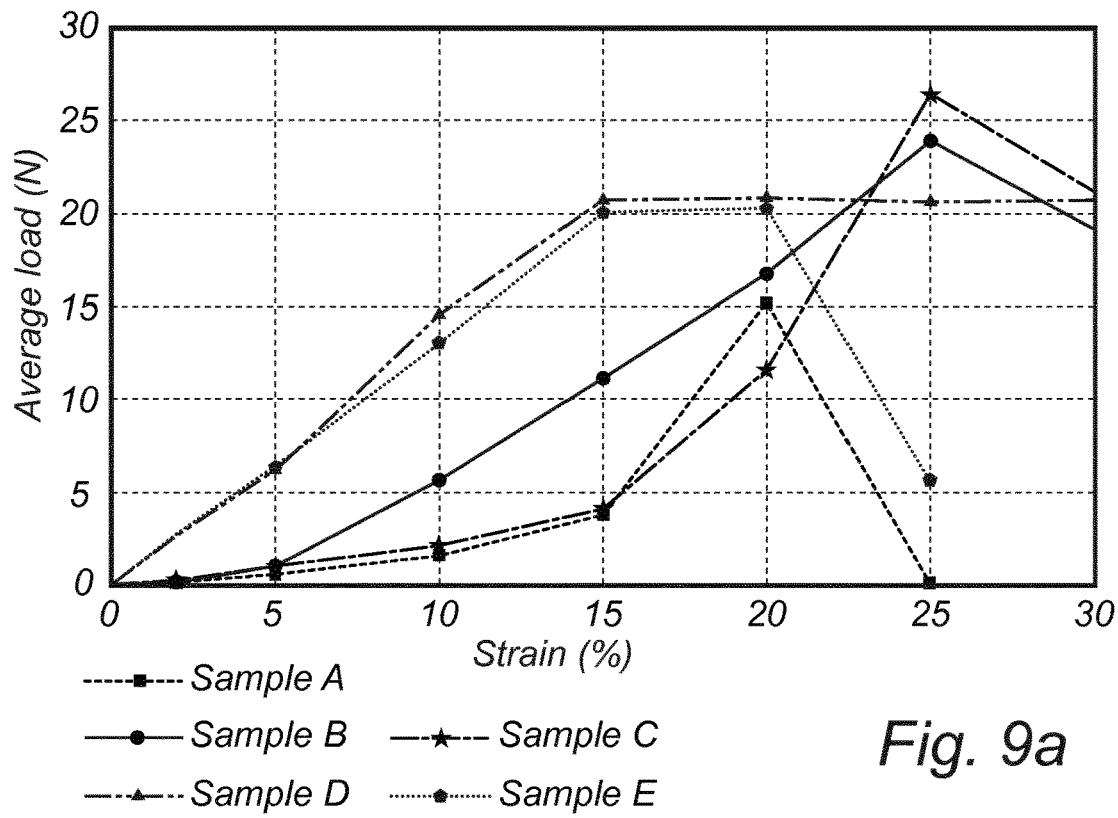
FIG. 9 illustrates the tensile curves for five different types of anisotropic layers in the second direction (y) (FIG. 9a) and in the first direction (x) (FIG. 9b).
Figure 9B:
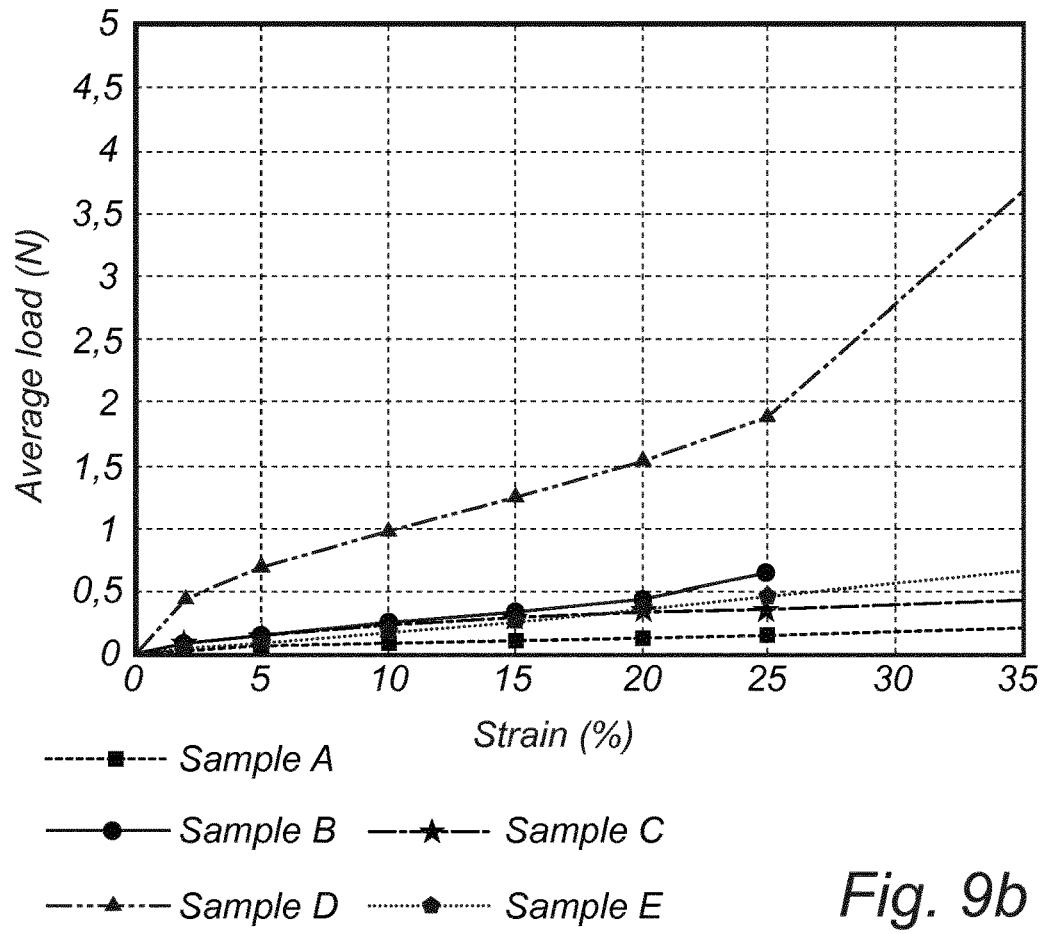

Five different anisotropic layers were tested, and their tensile curves are illustrated in FIG. 9. FIG. 9a illustrates the tensile curves in the second direction (y) and FIG. 9b illustrates the tensile curves in the first direction (x). Sample A was M33116-A (polyamide) from Eschler, sample B was M33116-B (polyamide) from Eschler, sample C was 322223 (polyester) from Eschler, sample D was 114160 Delstar (polyamide sample) from DEKA Medical, and sample E was a 40 gsm spunlace nonwoven comprising viscose and polyethylene (70:30).

Finite Element (FE) Modelling

The mechanisms leading to pressure ulcers are not fully understood. Pressure sensing mats can give information on pressure present at the mattress under the skin surface but does not inform on the behaviour inside the soft tissues, at the origin of damage. Therefore, the Finite Element (FE) method offers a great alternative to study the biomechanisms of action for pressure ulcers.

The FE method is a numerical and computational technique used to solve multiphysics problems by solving partial differential equations upon different types of discretizations. The FE method subdivides a large problem or large 3D model into smaller parts called finite elements. The analyses are performed within each elements and the assembly gives a solution to the entire problem.

The workflow for a FE analysis can be explained as follows: creation of a 3D model constituted of finite elements, definition of the material properties of the model, definition of the boundary conditions and loadings to apply to the model according to the problem, computational solving of the problem, and analysis of the results through visualization and calculations.

Finite Element (FE) Settings and Anatomical Model

In order to understand the effect of the dressing according to the present invention, finite Element (FE) models of a pelvis and of a dressing according to the invention were created and analyses were performed to study the effect of pressure and stresses on the skin and in deep tissue layers. The volunteer was a non-smoker healthy adult male of 31 years at the time of the study (year birth 1984, length: 183 cm, weight: 77 kg).

The FE models were prepared in prepared in ANSA 16.0.1 and 17.1.0 (BETA CAE) and the analysis performed in ABAQUS 14.0 (DASSAULT SYSTEM). The FE model of the pelvis was segmented from MRI scans of the pelvis in order to insure the best anatomical accuracy.

The soft tissues were represented as non-linear materials (the muscles were lumped together as one material, the fat and the skin were lumped together as one compressive material), the bones as rigid body. The deformation of the soft tissue caused by compression from the body weight was used to validate the FE model and its material properties with ABAQUS 14.0 (DASSAULT SYSTEM). The validation was carried out by comparing the thickness of the soft tissues before and after compression between the model and the MRI data.

The deformation of the soft tissue was performed by simulating a clinical setting where a patient is lying on a mattress. A soft mattress (30 kPa) was added under the pelvis and the equivalent of the body weight was applied to induce contact and compression of the pelvis on the mattress. The deformation of the soft tissue due to pure compression was simulated with a vertical displacement of the body on the mattress.

The following soft tissue layers were investigated for stress distribution, and the following stresses were analysed:

TABLE 1

| | Soft tissue layers and simulated stresses | |
|---|---|---|
| Soft tissue layer | Definition of soft tissue layer | Stresses in compression |
| At the skin | Posterior part of the skin/fat lump | Mean pressure |
| At the muscle | Posterior part of the muscle, interface between the muscle and the fat | Von Mises stresses, VMS |

"Stresses in compression" means the stresses that arise from compression; i.e. defined as the vertical displacement of the body on a mattress to mimic the compression of the pelvis when the patient is lying horizontally on a mattress.

The mean pressure (or hydrostatic stress) and the Von Mises stresses give an overview of the strain energy density and help to capture the origins of the strains and stresses in the tissues.

The Von Mises Stresses (VMS) are defined in the Distorsion Energy Theory and represent a common criterion widely used in engineering. The VMS can be defined as:

$$\sigma_{VM} = \sqrt{1/2[(\sigma_{xx}-\sigma_{yy})^2+(\sigma_{yy}-\sigma_{zz})^2+(\sigma_{zz}-\sigma_{xx})^2]+3(r_{xy}^2+r_{yz}^2+r_{zx}^2)}$$

Figure 10:
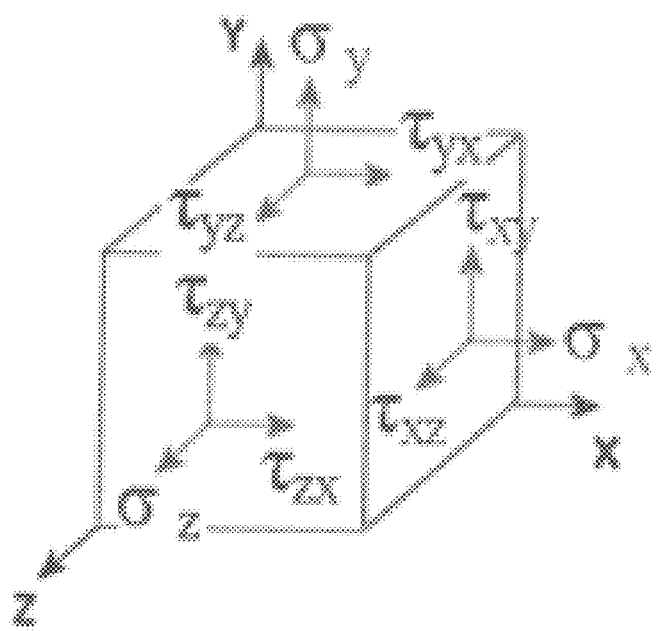
FIG. 10 illustrates the stress components in the Von Mises Stress equation.

The stress components for the Von Mises Stress equation are shown in FIG. 10.

The Mean Pressure (or hydrostatic stress) can be defined as:

$$\sigma Hyd = 1/3(\sigma xx + \sigma yy + \sigma zz)$$

The strain energy density is separated into different components in order to isolate the hydrostatic stresses and the deviatoric stresses. The deviatoric stresses are represented by the VMS and combine stresses in different directions into an equivalent stress that will take into account normal stresses, shear stresses and distortion. Combined with the hydrostatic stresses, the VMS can give an overview of the separate components of the strain energy density and help to capture the origins of the strains and stresses in the tissues.

The physical and mathematical relationship between force, stress, displacement and strain are the following:

Strain ε is defined as "deformation of a solid due to stress" and can be expressed as:

$$\varepsilon = dl/L_o$$

wherein
dl=change of length or displacement (mm)
$L_o$=initial length (mm)

The Young's modulus E (MPa) is a property of the material and can be defined as:

$$E = \sigma/\varepsilon$$

Shear stresses are stresses parallel to the plane and can be expressed as:

$$\tau = F_p/A$$

wherein
τ=shear stress (MPa)
$F_p$=parallel component force (N)
A=area (mm²)

There are no known values of critical stresses, as it varies between individuals, due to their physiological parameters, health, age and with the duration of exposure to the stresses. Therefore, the evaluation of the effect of the dressings relies on qualitative values. In the FIGS. 5-8, the black areas show higher stresses (critical values of stresses). Critical values of stresses have been defined as high value of stresses showing difference with "no dressing" and the dressings. The critical value of stresses correspond to about 1 kg for 10 cm2 (around 10 kPa).

Effect of Inventive Dressing

In the first set of simulations, a dressing according to the present invention comprising a foam pad and an anisotropic layer incorporated into the body contact layer was studied. The dressing according to the invention was created from technical CAD drawings and the simulated anisotropic layer refers to a shell with properties similar to a layer having a tensile force at 15% strain of 20.6 N in the second (y)

direction, and 0.3 N in the first (x) direction. The inventive dressing was compared with a dressing comprising only a foam pad, and with the scenario when no dressing was used. In the simulations, the skin-facing surface of the dressings was fully adherent to the skin.

The material properties of the different dressings were defined by actual laboratory measurements in tension and compression based on ASTM D 882-12 and ASTM D 3574-11.

Simulations were performed to analyse the stresses in compression (von Mises stresses) in the soft tissue layers muscle, and fat, respectively.

FIG. 5 illustrates the distribution of critical Von Mises stresses (black spots) at the muscles in the sacrum region after exposure to compression. FIG. 5a illustrates the critical von Mises stresses in the muscle when no dressing has been applied, FIG. 5b illustrates the critical Von Mises stresses when a dressing comprising a foam pad has been applied, and FIG. 5c illustrates the critical von Mises stresses when a dressing according to the present invention has been applied.

As can be seen in FIG. 5, the volume of muscle under critical VMS stress was substantially reduced when a dressing of the present invention was used.

Another way to evaluate the performance of the dressings is to define its ability to reduce the volume of tissue under critical stresses. Critical values of stresses are defined as high value of stresses showing difference with "no dressing" and the dressings. As mentioned, for the Von Mises Stresses, the critical value of stresses correspond to about 1 kg for 10 cm2 (around 10 kPa).

The performance of the dressing can therefore be defined as the percentage reduction of volume of tissue under critical stress when compared to no dressing:

$$\text{Reduction (\%)} = \frac{(V_{nd} - V_d)}{V_{nd}} \times 100$$

with Reduction (%)=percentage reduction of volume of tissue under critical stress with $V_{nd}$=Volume of tissue under critical stress with no dressing with $V_d$=Volume of tissue under critical stress with dressing The percentage of reduction of the volume of soft tissue (muscles) subject to critical VMS stresses is summarized below.

TABLE 2

Percentage reduction of volume of muscle under critical VMS stress

| | Foam pad | Inventive dressing |
|---|---|---|
| Reduction of volume of muscle under critical VMS stress | 56.4% | 79.8% |

As illustrated in table 2, the volume of muscle under critical VMS stress was substantially reduced when a dressing of the present invention was used.

In the second set of simulations, two different types of gel based dressings were simulated. The general construction of the simulated dressings is illustrated in FIG. 6. The dressing 600 comprised a gel pad 601, wherein the gel had a Youngs modulus of 8 kPa, except for in the coccyx region 602 of the pad, where the Youngs modulus was 6 kPa. Apertures 603 were provided in the central zone of the dressings, and an intermediate, isotropic layer was inserted to the gel (to stabilize for the low compressibility of the gel). Both dressings comprised an anisotropic layer having a tensile force at 15% strain of 20.6 N in the second (y) direction, and 0.3 N in the first (x) direction. The difference between the two gel based dressings was the location of the anisotropic layers: in the middle of the dressing (referred to as Gel dressing A), and in the body contact layer; i.e. in close proximity of the skin (referred to as Gel dressing B).

FIG. 7 illustrates the critical hydrostatic stress (mean pressure) distribution at the skin in the sacrum region after exposure to pressure and compression for Gel dressing A (FIG. 7b), Gel dressing B (FIG. 7c) compared to when no dressing was used (FIG. 7a). As can be observed, the anisotropic layer reduces the critical compression stresses at the skin compared to when no dressing is used. Surprisingly, this effect is remarkably enhanced when the anisotropic layer is incorporated into the body contact layer; i.e. when the anisotropy is localized in close proximity of the skin (FIG. 7c). Nearly all critical hydrostatic stresses are reduced with the inventive dressing.

The effect was also analysed deeper in the soft tissue; i.e. at the muscle. FIG. 8 illustrates the distribution of critical VMS stresses at the muscle (shown as black spots) when no dressing has been used (FIG. 8a) compared to Gel Dressing A (FIG. 8b) and Gel dressing B (FIG. 8c). As can be seen, the anisotropic layer remarkably reduces the critical VMS stresses, and the protective effect on soft tissue is further enhanced when the anisotropic layer is arranged close to the skin (in the body contact layer) as illustrated in FIG. 8c.

The effect of the dressing can also be represented as a calculation of the volume of soft tissue (muscle) subject to critical VMS stresses, as illustrated in table 3 below.

TABLE 3

Percentage reduction of volume of muscle under critical VMS stress with gel dressings A and B

| | Gel dressing A compared to no dressing | Gel dressing B compared to no dressing |
|---|---|---|
| % reduction of volume of muscle under critical VMS stress | 88.2% | 99.2% |

Other embodiments of the invention will be apparent to those skilled in the art from consideration of the specification or practice of the invention disclosed herein. It is intended that the specification and examples be considered as exemplary only, with the true scope of the invention being indicated by the following claims.

The invention claimed is:

1. A medical dressing comprising a backing layer, a pad, and a body contact layer, wherein the pad is arranged between the backing layer and the body contact layer, and wherein the backing layer and the body contact layer extend beyond the periphery of the pad to define a border portion around the contour of the pad, wherein the body contact layer comprises an adhesive skin contact layer and an anisotropic layer having a first (x) direction and a second (y) direction perpendicular to the first (x) direction, wherein the anisotropic layer is stiffer in the second (y) direction than in first (x) direction, wherein the anisotropic layer has a tensile force at 15% strain in the second (y) direction that is at least 6 times higher than in the first (x) direction, as measured by the tensile test ASTM D882-12.

2. The medical dressing according to claim 1, wherein the body contact layer further comprises a plastic film.

3. The medical dressing according to claim 2, wherein the plastic film comprises polyurethane.

4. The medical dressing according to claim 1, wherein the body contact layer comprises a plurality of apertures.

5. The medical dressing according to claim 4, wherein the plurality of apertures are selected from a plurality of elongated cuts or elongated openings, wherein each elongated cut or elongated opening has a length direction and a width direction, and wherein the length direction is the same as or parallel with the second direction (y).

6. The medical dressing according to claim 1, wherein the dressing comprises a second anisotropic layer being stiffer in the second (y) direction than in the lateral direction (x).

7. The medical dressing according to claim 6, wherein the second anisotropic layer has a tensile force at 15% strain in the second (y) direction that is at least 6 times higher-than in the lateral direction (x), as measured by the tensile test ASTM D882-12.

8. The medical dressing according to claim 1, wherein the anisotropic layer has a tensile force at 15% strain in the second (y) direction of at least 4 N as measured by the tensile test ASTM D882-12.

9. The medical dressing according to claim 1, wherein the anisotropic layer comprises a nonwoven.

10. The medical dressing according to claim 1, wherein the adhesive skin contact layer comprises a silicone gel.

11. The medical dressing according to claim 1, wherein the dressing comprises at least one gripping tab; the gripping tab being coplanar with and projecting outwardly from the border portion of the dressing.

12. A method comprising:
a) applying the medical dressing according to claim 1 to a subject at an area of risk of developing a pressure ulcer, thereby reducing the risk of the development of a pressure ulcer at the area of risk of developing a pressure ulcer.

13. A medical dressing comprising a backing layer, a pad, and a body contact layer, wherein the pad is arranged between the backing layer and the body contact layer, and wherein the backing layer and the body contact layer extend beyond the periphery of the pad to define a border portion around the contour of the pad, wherein the body contact layer comprises an adhesive skin contact layer, a plastic film, and an anisotropic layer having a first (x) direction and a second (y) direction perpendicular to the first (x) direction, wherein the anisotropic layer is stiffer in the second (y) direction than in first (x) direction, wherein the plastic film is arranged between the anisotropic layer and the adhesive skin contact layer.

14. A medical dressing comprising a backing layer, a pad, and a body contact layer, wherein the pad is arranged between the backing layer and the body contact layer, and wherein the backing layer and the body contact layer extend beyond the periphery of the pad to define a border portion around the contour of the pad, wherein the body contact layer comprises an adhesive skin contact layer, a plastic film, and an anisotropic layer having a first (x) direction and a second (y) direction perpendicular to the first (x) direction, wherein the anisotropic layer is stiffer in the second (y) direction than in first (x) direction, wherein the anisotropic layer is arranged between the adhesive skin contact layer and the plastic film.

\* \* \* \* \*